Figure 1:
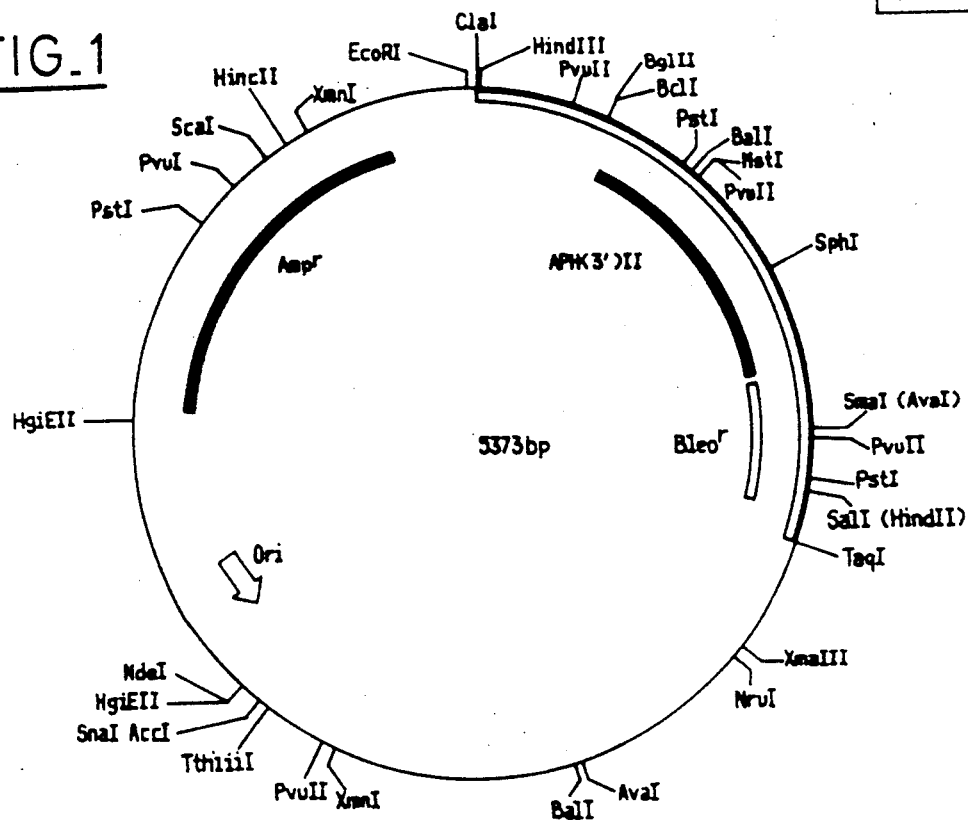

United States Patent [19]

Armau et al.

[11] Patent Number: 5,021,344
[45] Date of Patent: Jun. 4, 1991

[54] APPLICATION OF ANTIBIOTICS OF THE PHLEOMYCIN FAMILY AS SELECTION AGENT IN THE FIELD OF GENETIC ENGINEERING

[75] Inventors: Elise Armau; Daniel Drocourt; Gilles Etienne; Gérard Tiraby, all of Toulouse, France

[73] Assignee: Centre National de la Recherche Scientifique (CNRS), Paris, France

[21] Appl. No.: 864,726

[22] PCT Filed: Aug. 30, 1985

[86] PCT No.: PCT/FR85/00234
§ 371 Date: Apr. 30, 1986
§ 102(e) Date: Apr. 30, 1986

[87] PCT Pub. No.: WO86/01537
PCT Pub. Date: Mar. 13, 1986

[30] Foreign Application Priority Data

Aug. 31, 1984 [FR] France ............... 84 13502

[51] Int. Cl.⁵ ............ C12N 15/70; C12N 15/64; C12N 15/74; C12N 15/79
[52] U.S. Cl. .................. 435/172.3; 435/34; 435/69.1; 435/70.1; 435/71.1; 435/91; 435/172.1; 435/240.2; 435/240.3; 435/254; 435/320.1; 435/839; 435/849; 435/878; 435/942; 935/9; 935/22; 935/55; 935/59; 935/66; 935/69; 935/70; 935/72; 935/73; 935/74
[58] Field of Search ............ 435/68, 91, 34, 172.1, 435/172.3, 240.2, 253, 254, 255, 256, 320, 849, 886, 940; 536/27; 935/9, 22, 23, 24, 28, 29, 59, 69, 72, 73, 74, 79, 84

[56] References Cited

FOREIGN PATENT DOCUMENTS 0035831 9/1981 European Pat. Off. .
0093611 11/1983 European Pat. Off. .

OTHER PUBLICATIONS

Jimenez et al, *Nature*, 287:869–871 (1980).
Maniatis et al, 1982, Molecular Cloning–Cold Spring Harbor Laboratory, pp. 11–13.
Suzuki et al, 1969, *J. Antibiotics* 22(9):446–448.
Putnoky et al. 1983, *Mol. Gen. Genet.* 191:288–294.
Gritz et al, 1983, *Gene*, 25:179.
Takeshi Murakami et al, "Cloning of Anti-biotic Resistance Genes in Streptomyces", *Journal of Antibiotics*, vol. 36, No. 10, Oct. 1983, pp. 1305–1311.
Yasutoshi Takeichi et al, "Cloning of Bacillus Subtilis Alpha-Amylase Structural Gene in Plasmid pUB110", *Agric. Bid. Chem.*, vol. 47, No. 1, Jan. 1983, pp. 159–161.
P. Attfield et al., "R Plasmids Mediate Protection and Sensitivity to Bleomycin", *J. Pharm. Pharmacol.* 1980, 32 (Suppl.), p. 31p.
Takado Iijima et al., "Mutability of the Phleomycin Resistant Mutants of Bacillus Subtilis. I. Isolation of Genetically Unstable Mutants," *J. Gen. Appl. Microbiol.*, 1970, vol. 16, No. 5, pp. 419–427.

Primary Examiner—Robin L. Teskin
Assistant Examiner—Richard C. Peet
Attorney, Agent, or Firm—Wegner, Cantor, Mueller & Player

[57] ABSTRACT

A method of transforming eukaryotic or prokaryotic hosts sensitive to an antibiotic of the phleomycin family to confer resistance to the antibiotic is disclosed in which a phleomycin resistance gene is used as a selectable marker.

1 Claim, 6 Drawing Sheets

```
              10        20        30        40        50        60

TTCGAAATGACCGACCAAGCGACGCCCAACCTGCCATCACGAGATTTCGATTCCACCGCC
AAGCTTTACTGGCTGGTTCGCTGCGGGTTGGACGGTAGTGCTCTAAAGCTAAGGTGGCGG 70        80        90        100       110       120

GCCTTCTATGAAAGGTTGGGCTTCGGAATCGTTTTCCGGGACGCCGGCTGGATGATCCTC
CGGAAGATACTTTCCAACCCGAAGCCTTAGCAAAAGGCCCTGCGGCCGACCTACTAGGAG 130       140       150       160       170       180

CAGCGCGGGGATCTCATGCTGGAGTTCTTCGCCCACCCCGGGCTCGATCCCCTCGCGAGT
GTCGCGCCCCTAGAGTACGACCTCAAGAAGCGGGTGGGGCCCGAGCTAGGGGAGCGCTCA 190       200       210       220       230       240

TGGTTCAGCTGCTGCCTGAGGCTGGACGACCTCGCGGAGTTCTACCGGCAGTGCAAATCC
ACCAAGTCGACGACGGACTCCGACCTGCTGGAGCGCCTCAAGATGGCCGTCACGTTTAGG 250       260       270       280       290       300

GTCGGCATCCAGGAAACCAGCAGCGGCTATCCGCGCATCCATGCCCCCGAACTGCAGGAG
CAGCCGTAGGTCCTTTGGTCGTCGCCGATAGGCGCGTAGGTACGGGGGCTTGACGTCCTC 310       320       330       340       350       360

TGGGGAGGCACGATGGCCGCTTTGGTCGACCCGGACGGGACGCTCCTGCGCCTGATACAG
ACCCCTCCGTGCTACCGGCGAAACCAGCTGGGCCTGCCCTGCGAGGACGCGGACTATGTC 370       380       390       400       410       420

AACGAATTGCTTGCAGGCTACTCATGAGTGTGTCTTCCCGTTTTCCGCCTGAGGTCACTG
TTGCTTAACGAACGTCCGATGAGTACTCACACAGAAGGGCAAAAGGCGGACTCCAGTGAC 430       440       450       460       470       480

CGTGGATGGAGCGCTGGCGCCTGCTGCGCGACGGCGAGCTGCTCACCACCCACTCGAGCT
GCACCTACCTCGCGACCGCGGACGACGCGCTGCCGCTCGACGAGTGGTGGGTGAGCTCGA
```

FIG. 2

APPLICATION OF ANTIBIOTICS OF THE PHLEOMYCIN FAMILY AS SELECTION AGENT IN THE FIELD OF GENETIC ENGINEERING

The present invention relates to the application of phleomycins as a selection agent in the field of genetic engineering.

For bacteria there are available at the present time reliable and sensitive selection markers which are constituted by characters of resistance to certain antibiotics such as ampicillin, on the other hand, for eucaryotic cells the selection labelers are, generally, insensitive or require the use of a complicated technology to be usable.

It is, in addition, interesting to have available a selection labeler which can be expressed both in prokaryotic cells and in eukaryotic cells since often the vector constructions in the eukaryotic cells are partly effected in prokaryotic cells.

The present invention rests on the demonstration of new selection labelers which confer on the cells a resistance to antibiotics of the phleomycin type.

The present invention relates to the application of antibiotics of the phleomycin family as selection agent of cells which have been artificially modified by incorporation of a phleo$^r$ gene of resistance to an antibiotic of the family of phleomycins.

By "antibiotic of the family of phleomycins" is meant to denote, besides the phleomycins themselves, related antibiotics such as bleomycins, zorbamycins, victomycin, platomycins, tallysomycins or the antibiotics SF 1771, SF 1961 and YA 56, as well as mixtures of these antibiotics.

These antibiotics are characterized by a basic structure which differentiates them distinctly from the other antibiotics and the tests carried out within the scope of the present invention have demonstrated that the exact nature of the antibiotic used for the selection does not notably modify the result obtained provided that the antibiotic is indeed of the phleomycin type.

These antibiotics obtained commercially (bleomycine) or prepared from productive strains ATCC 21890 and 21892 (phleomycins), ATCC 21807 (victomycine), ATCC 21893 (platomycines), ATCC 31158 (tallysomycines), ATCC 31248 (SF 1771) are relatively toxic for bacteria, the lower eukaryotics like the yeasts and the fungi and the higher eukaryotics both animal and plant cells in cultivation.

Recently isolated strains of Actinomycetes produce antibiotics identical with those mentioned above or different. Particularly, the strain V9, Streptoverticillium in the course of taxonomic identification, synthesizes substances belonging to the family of phleomycines. The absorption curves in the ultra-violet of the purified products of the V9 strain are significantly different from those of the products mentioned above.

The genes which confer resistance on antibiotics of the phleomycin type are named below generically as phleo$^r$ genes.

It should be pointed out that up to the present numerous distinct phleo$^r$ genes have been established as will be demonstrated below.

The phleo$^r$ genes are borne by natural plasmids isolated from bacterial strains, for example found in a hospital environment, or can be cloned from the DNA of various organisms, particularly the DNA of organisms producing antibiotics of the phleomycin type. But these phleo$^r$ genes also exist in genetic materials widely available since it has been possible to establish the presence of such a gene on the transposon Tn5 of Escherichia coli or on the plasmid pUB110.

A gene of great importance for the present invention is that borne by the transposon Tn5 to E. coli well known to molecular biologists. This gene whose function has not yet been described is situated in the central portion of Tn5, between the gene which results in the resistance among others to kanamycin and that which results in the resistance in certain bacteria to streptomycin.

The exact location of the gene concerned, denoted by Tn5 phleo$^r$, has been determined exactly by dissection of the Tn5 DNA with various restriction enzyme and by determination of the corresponding nucleotidic sequence.

The phleo$^r$ Tn5 gene results in the resistance to all the antibiotics mentioned above, including here those of the V9 strain, when the latter is rendered functional after attachment of suitable promoter and terminal sequences of the carrier organism.

Thus the phleo$^r$ Tn5 gene alone is functional in Gram$^-$ bacteria and in Gram $+$ bacteria like for example the bacilli and the streptomyces.

The phleo$^r$ Tn5 gene results also in the resistance to these antibiotics in yeasts, to animal and vegetable cells in cultivation when the latter contain the functional gene.

A second gene worthy of interest is borne by the plasmid pUB110 well known to geneticians of the bacilli. This gene is situated on the plasmid pUB110 downstream of the gene which confers the resistance to tobramycin. It is comprised in a region bounded by the BglII site and which ends in anticlockwise direction to the BamHI site.

This gene named phleo$^r$ 110 results in resistance to all the antibiotics mentioned previously in bacilli bearers of the plasmid pUB110 and also in Gram$^-$ bacteria when the gene is placed under the dependence of suitable promoter and terminal sequences.

By analogy with the example of the phleo$^r$ Tn5 gene the phleo 110 gene should also be expressed in the environments of lower and higher eukaryotes after attachments to the sequences specific to each organism.

A third source of resistance genes to antibiotics of the family of phleomycins is provided by bacteria producers of these antibiotics.

A gene denoted phleo$^R$ SV present on the chromosomic DNA of the SV strain has been cloned on a streptomyces plasmid. The phleo$^R$ SV gene situated on the hybrid plasmid pUT212 confers the resistance to the antibiotics of the family of phleomycin, to the Streptomyces violaceoniger strain which harbors the plasmid.

The physical maps of the genes Tn5 phleo$^r$, 110 phleo$^r$ and SV phleo$^r$ determined by various restriction enzymes are dissimilar, which indicates a very great divergence between the three genes.

The employment of the antibiotics of the family of phleomycins, which will sometimes be called below phleomycins for simplification, as selection agent may be done according to modalities known in the field of genetic engineering.

Thus, when the technique employs autoreplicating vectors such as plasmids, phages or viruses, the selection agent is generally used positively or negatively.

It is possible thus to amount to a process of selection of a transformed or transfected cell by a cloning and/or expression vector of a determined protein, characterized in that there is introduced into this vector a phleo$^r$ gene of resistance to an antibiotic of the family of phleomycins as well as the elements possibly necessary to ensure its expression into the cells concerned, and in that, after transformation or transfection, cells obtained are subjected to the action of an antibiotic of the family of phleomycins and in that the resistance cells are selected.

It may also amount to a process of selection of transformed or transfected cells by a cloning and/or expression vector of a particular protein which has integrated a DNA segment, characterized in that a DNA segment is introduced into the phleo$^r$ gene of resistance to the antibiotic of the family of phleomycins borne by said vector and the transformed or transfected cells are subjected to the action of an antibiotic of the family of phleomycins and the sensitive cells are selected.

This second process obviously necessitates having preserved an original of the culture to be able to take up therefrom, the sensitive colonies.

These processes are well known in principle, however when, the cells employed are eucaryotic cells, the yields of selection with labelers of the prior art are often rather low and necessitate the use of large amounts of the selection agent, which in certain cases only ensures a very low selection margin.

On the contrary, the use of the phleomycins permits a selection both in prokaryotes and in eukaryotes with small amounts of selection agent and with very high sensitivity.

By way of example, in the case of the yeast *Saccharomyces cerevisiae*, the strain transformed by a vector bearing the phleo$^r$ gene resists to considerable concentrations of bleomycins, 100 times greater than those supported by the untransformed strain.

Generally, the selection agent will use concentrations comprised between 0.1 and 100 γ in the culture medium of the modified cells.

Thus, it has been possible to establish the action of the selection agents, both in Gram− and Gram+ bacteria, and in yeasts, fungi or animal or vegetable cells.

In addition, although it is interesting to insert the phleo$^r$ gene in a vector, it is also possible to integrate this gene into a cellular chromosome in order to confer on the cell a resistance to the phleomycins.

Of course, the structure of the previously mentioned vectors does not constitute in itself a characteristic of the present invention and these vectors may be prepared by known techniques. It is besides evident that a certain number of vectors existing at present could be adapted by inserting the phleo$^r$ gene so as to be able to be manipulated by using the selection agents of the present invention.

The elements necessary to ensure the expression of the phleo$^r$ gene depend, of course, on the host cell, but are known to the man skilled in the art; the examples below will demonstrate besides certain elements enabling the expression of phleo$^r$ gene to be ensured according to the nature of the host.

Figure 3:
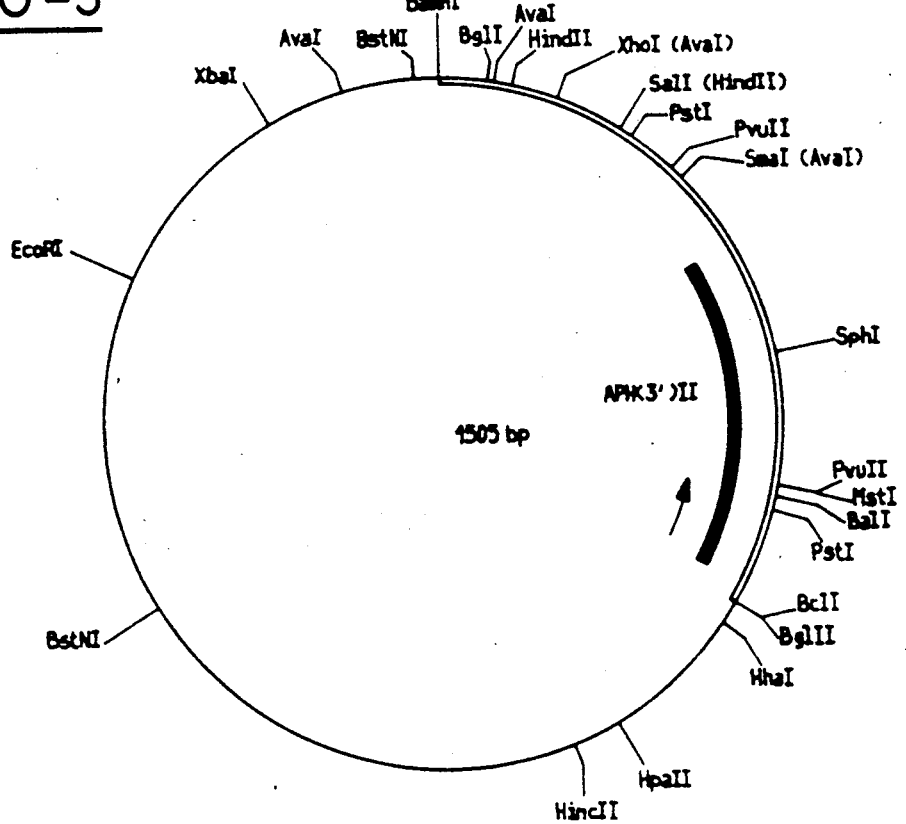
Figure 4:
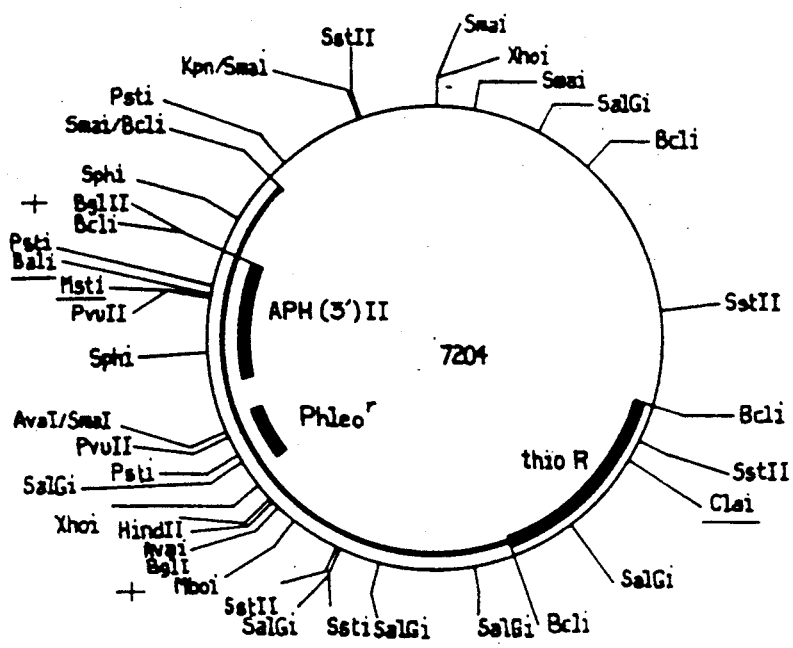
Figure 5:
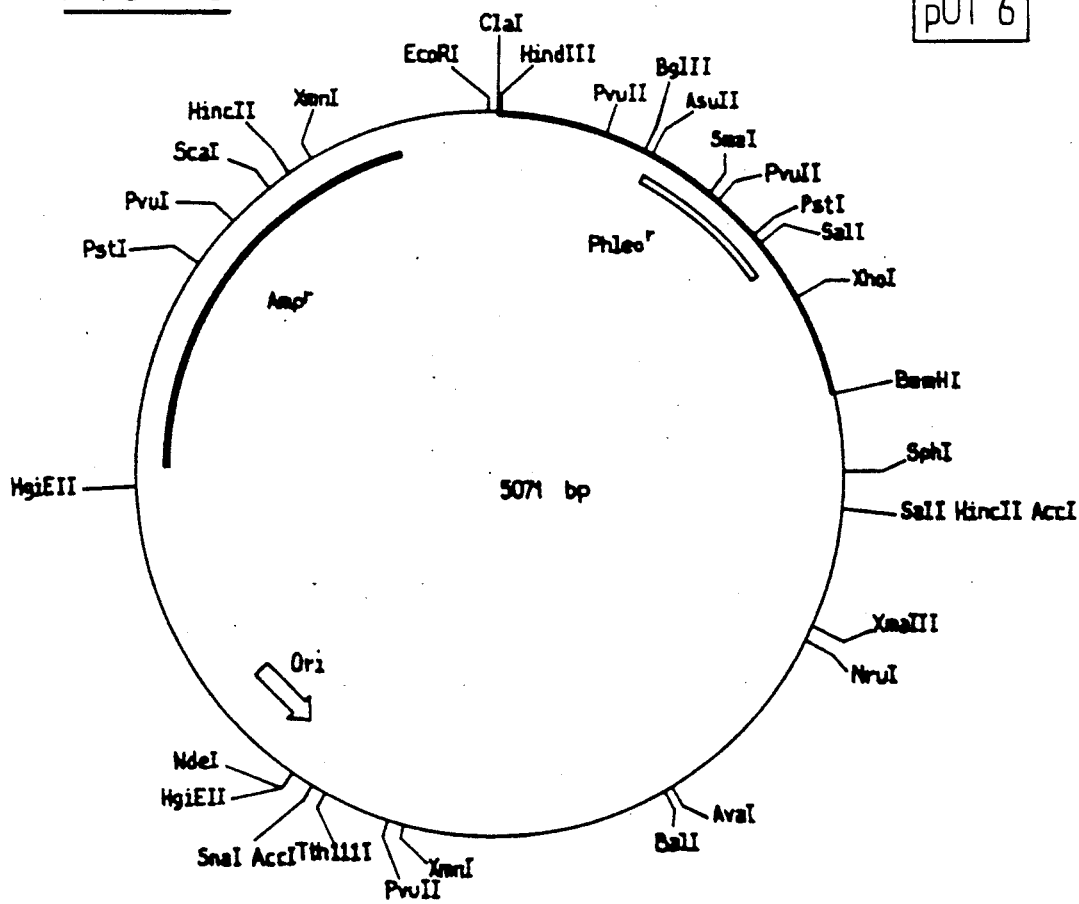
Figure 6:
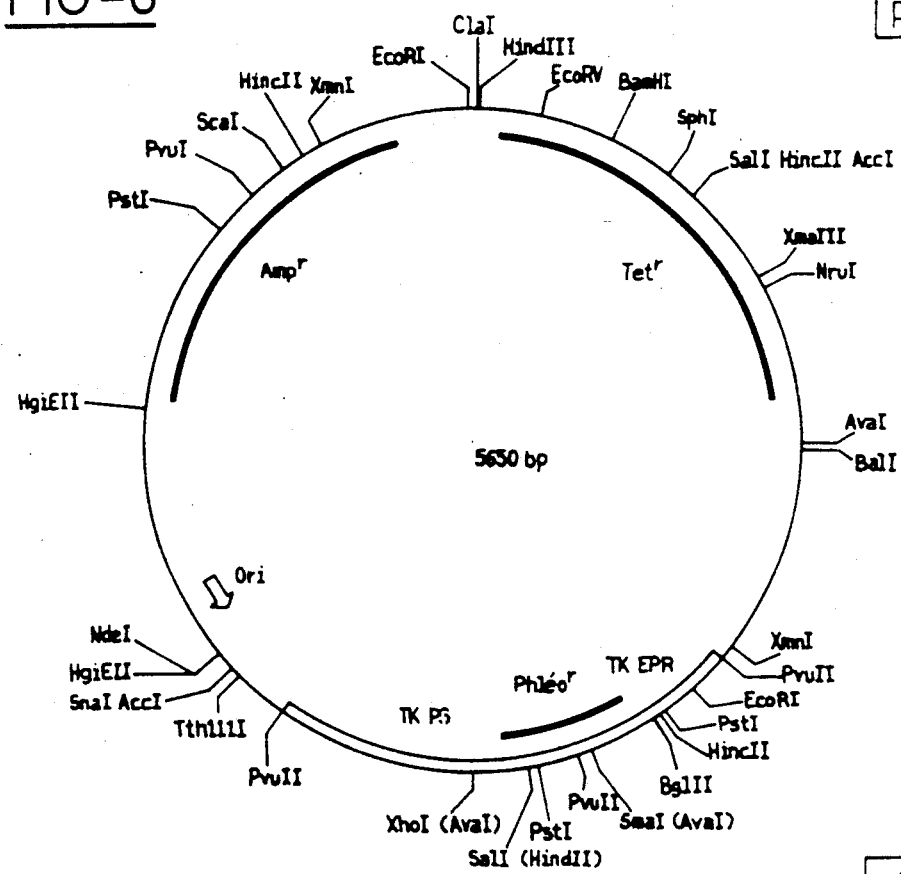
Figure 7:
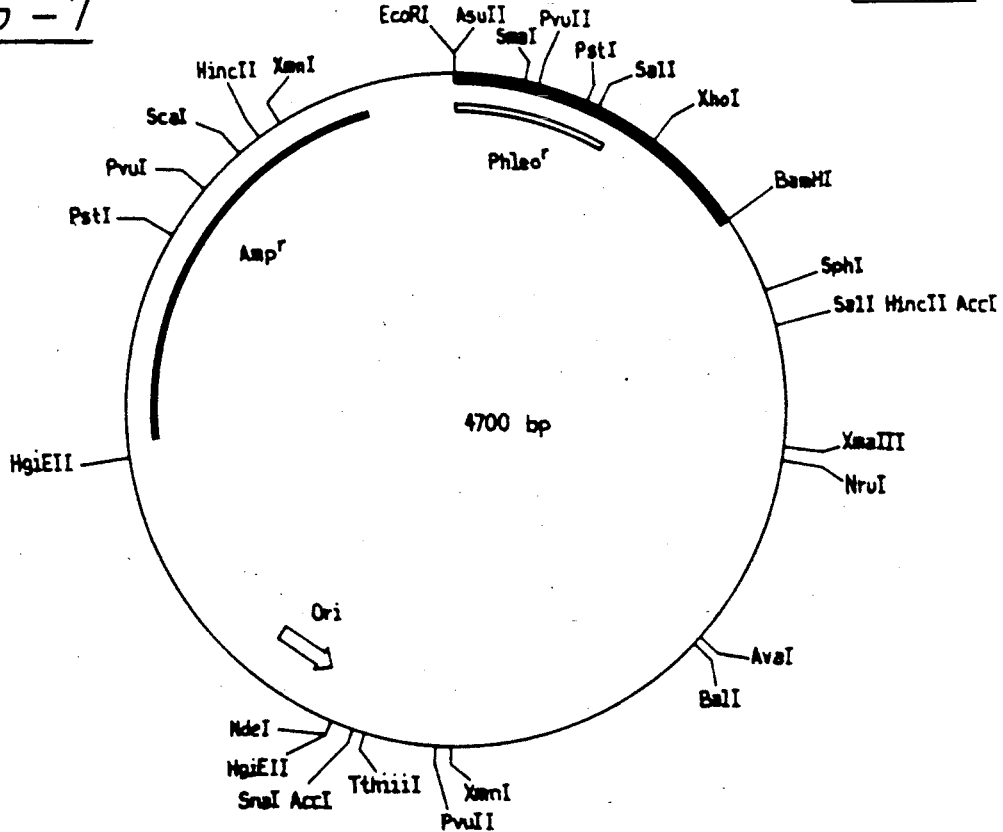
Figure 8:
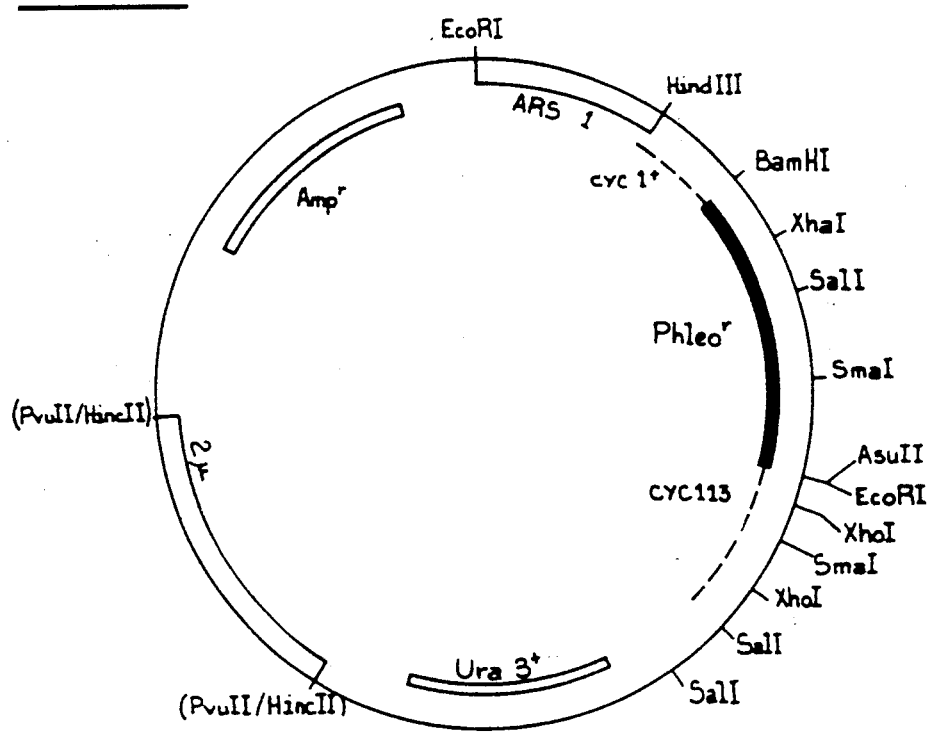
Figure 9:
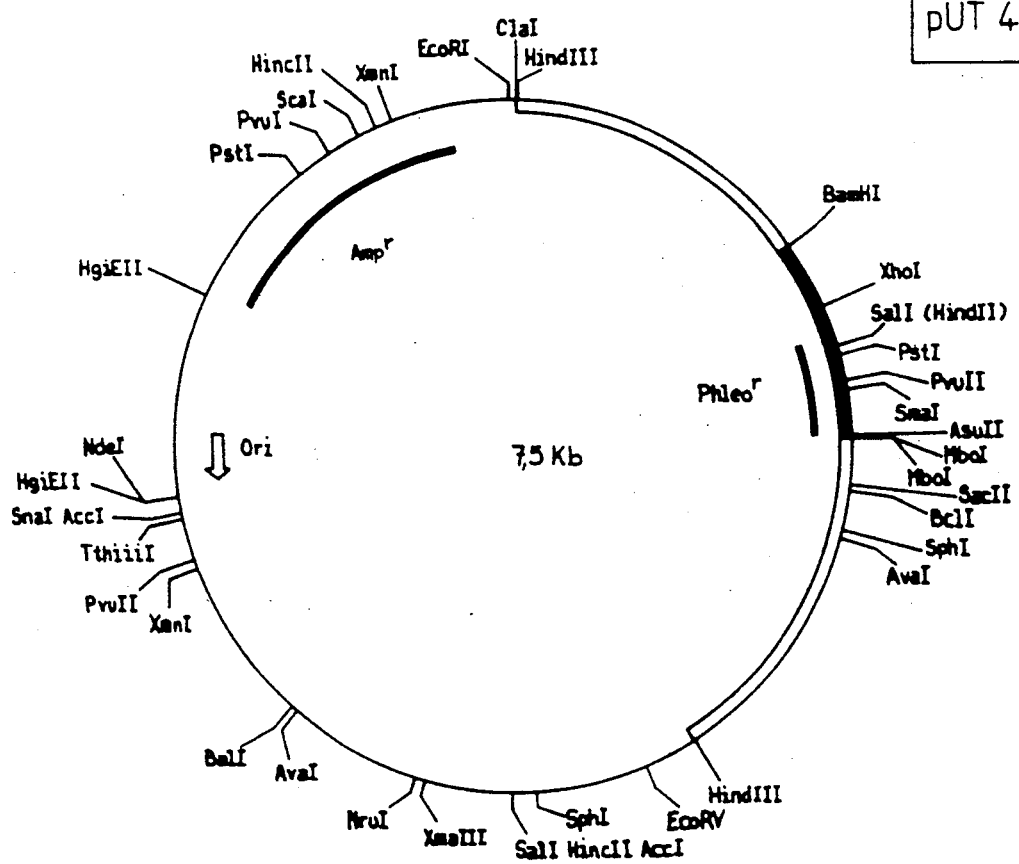
Figure 10:
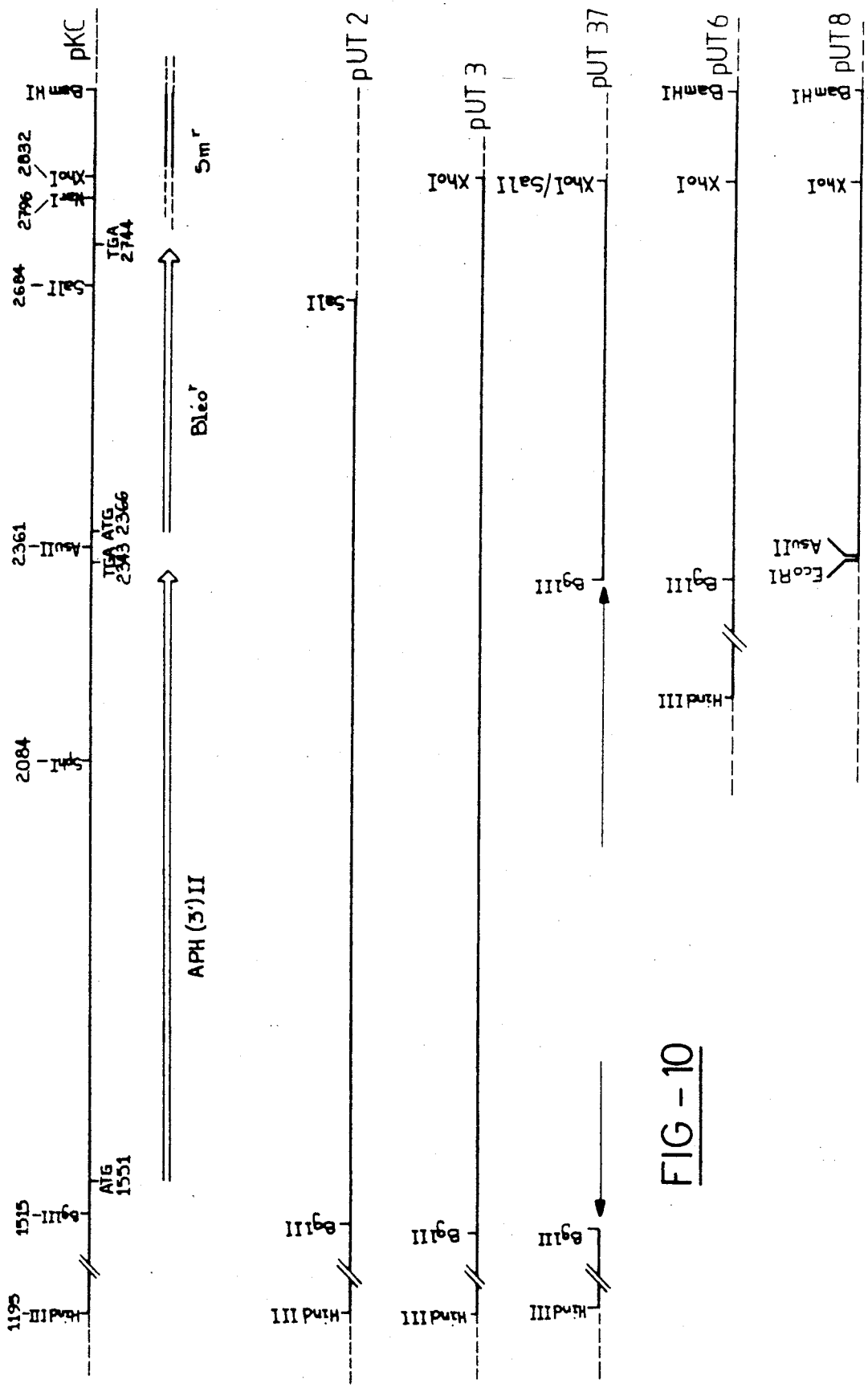

These examples will be described by referring to the figures in which:

FIG. 1 is a diagram of the plasmid pUT3,

FIG. 2 shows a nucleotidic sequence of the phleo$^r$ gene of the transposon Tn5, FIG. 3 is a diagram of the plasmid pUT100, FIG. 4 is a diagram of the plasmid pUT201, FIG. 5 is a diagram of the plasmid pUT6, FIG. 6 is a diagram of the plasmid pUT66, FIG. 7 is a diagram of the plasmid pUT8, FIG. 8 is a diagram of the plasmid pUT301, FIG. 9 is a diagram of the plasmid 400, FIG. 10 shows diagramatically the restriction fragments of pKC7 employed in the examples.

The abbreviations used in these figures are considered as known or will be explained in the description.

Except for indication to the contrary, the various processes and products mentioned are employed according to techniques which are known and/or recommended by the manufacturer.

EXAMPLE I

Cultures in a Petri dish are prepared from Actinomycetes strains producing antibiotics belonging to the group of Bleomycins, obtained from the American Type

| Culture Collection: | |
|---|---|
| *Streptomyces verticillus* | ATCC 15003 (Bleomycins) |
| *Streptomyces verticillus* | ATCC 21678 (Bleomycins) |
| *Streptomyces verticillus* | ATCC 21890 (Phleomycins) |
| *Streptomyces flavoridis* | ATCC 21892 (Phleomycins) |
| *Stretoalloteichus hindustanus* | ATCC 31158 (Tallysomycins) |
| *Streptosporangium violaceo-chromogenes* sub. sp. *globophilum* | ATCC 21893 (Platomycins) |
| *Streptosporangium violaceochromogenes* | ATCC 21807 (Victomycins) |
| *Streptomyces toyocaensis* | ATCC 31248 (S.F. 1771) |

The surface of the dishes containing 30 ml of GAPY (glucose 10; soluble starch 20; yeast extract 5; soja peptone 5; CaCo$_3$1; gelose 15 g/l per 1 l of distilled water) is seeded by a platinum loop with a suspension of mycelia spores of the above strains. The production of the antibiotics is estimated after 15 days of incubation at 27° C. in the following manner: a gelose cylinder is taken up from the dish of the production medium then deposited on a medium (antibiotic n°2 DIFCO+2 g/l glucose, pH 8) seeded in depth with bacteria of the strain HB101 of *Escherichia coli*. In this example two indicating strains are used: HB101 and HB101 containing the plasmid pKC7 (RAO et al., Gene 7, 79, 1979). The plasmid pKC7 isolated from the strain ATCC 37084 was introduced by a transformation in the strain HB101.

The results of the antibiogram expressed in inhibition diameter (mm) are shown in table 1.

TABLE 1

Determination of the sensitivity of two isogenic strains of *Escherichia coli* to the antibiotics of the family of bleomycins

| Indicating Strains | Producing Strains | | | | | | | |
|---|---|---|---|---|---|---|---|---|
| | 15003 | 21678 | 21890 | 21892 | 31158 | 21893 | 21807 | 31248 |
| HB 101 | 31 | 32 | 17 | 18 | 37 | 28 | 16 | 14 |
| HB 101 (pKC7) | 6 | — | — | — | 20 | — | — | — |

It emerges from this table that the plasmid pKC7 protects the cells which harbor it against all the antibiotics of the family of bleomycins examined in this example. The strain 31158 producing tallysomycins also synthesizes antibiotics of the aminoside type among which are particularly apramycin. The apramycin tested by the method of discs (50 μg) gives an inhibition aureola of 30 mm identical for the two *Escherichia coli* strains. The inhibition observed for the strain HB101 (pKC7) by the gelose cylinders of the strain 31158 is due to the presence of the apramycin.

EXAMPLE II

The gelose medium corresponding to 20 Petri dishes incubated for 10 days, of production medium of the strain *Streptoalloteichus hindustanus* (ATCC 31158) is ground twice by means of a ultraturax in the presence each time of 200 ml of water then centrifuged at 5000 rpm. The supernatant liquor is filtered, then passed into a column of resin IRC-50 previously equilibrated with trifluoroacetic acid (0.1N). The tallysomycins present in the supernatant liquor are absorbed on the resin whereas all the aminosides (nebramycins, tobramycin and apramycin) are not retained. After washing with water, the tallysomycins are detached with 0.01N trifluoroacetic acid. The volume of the eluate is reduced to half by evaporation under reduced pressure and the pH brought to 7. The resulting solution kept at 4° C. is the solution of tallysomycins used in the remainder of the tests. The cellulose disc inbibed with 20 μl of this solution gives an inhibition aureola of 33 with HB101 and no inhibition with HB101 (pKC7) under the conditions described in example I.

A bleomycin solution constituted principally of the component A5 is prepared in identical fashion from 20 dishes of the *Streptomyces verticillus* (ATCC 21678) strained supplemented for this strain with 100 μg/ml spermidine. A cellulose disc soaked with 20 μl of this A5 bleomycin solution gives an inhibition aureola of 35 with HB101 and does not give an inhibition with HB101 (pKC7).

EXAMPLE III

The productivity of the strain ATCC 21890 of *Streptomyces verticillus* being low in stirred liquid cultures, a genetic improvement of the strain was effected by two mutagenic treatments and selection by the method of the gelose cylinder.

Strain 21890→A 152-1→B-81 C

| ultra-violet light | nitroso-guanidine |
| --- | --- |

The mutant strain B-81 C was used for a production of phleomycins in liquid culture: an Erlenmeyer flask of 300 ml containing 40 ml of the inoculum medium (soluble starch: 10; yeast extract: 5; acid casein hydrolysate: 5; meat extract: 3; glucose: 1; $MgSO_4$: 0.5; $KH_2PO_4$: 0.2; $NaHPO_4$: 0.2; $CaCO_3$: 0.5; g per liter, pH 7 before sterilization) is seeded with 0.5 ml of a suspension of mycelium-spores prepared from a dish of GAPY medium of the mutant strain B-81 C of Streptomyces verticillus. After 40 hours of incubation at 27° C. on the rotary stirrer (220 rpm) 5 ml of the inoculum culture were used to inoculate an Erlenmeyer flask of 2 liters containing 200 ml of the production medium (soluble starch: 20; glucose: 10; Pharmamedia: 10; soluble corn extract: 10; ammonia sulfate: 3; $CaCO_3$: 4 g per liter, pH 6.5 before sterilization). After 7 days of fermentation at 27° C. on a rotary stirrer (250 rpm/min) the culture corresponding to 5 Erlenmeyer flasks is filtered. The filtrate (900 ml) is passed into a colony (40 cm×2 cm) of IRC-50 resin previously equilibrated with trifluoroacetic acid (0.1N). After washing with 1 liter of distilled water the phleomycins are eluted with 300 ml of 0.02N trifluoroacetic acid. The neutralized eluate is passed directly over a column (30×2 cm) of XAD-2 resin previously equilibrated with water. After washing the column with 250 ml of distilled water, the phleomycins are eluted with 100 ml of 80% methanol in 0.1N HCl. The eluate evaporated to dryness gives 210 mg of a blue powder constituted principally of phleomycins complexed with $Cu^{++}$. The powder obtained by this procedure is free from antibiotic active on Gram+ bacteria distinct from bleomycins and from the polyenic antifungic agent produced conjointly by the strain 21890 and its mutants. The activity of the phleomycin powder is compared with that of bleomycin marketed by the Laboratoires Roger Bellon (France) and the pepleomycin under clinical testing (Laboratoires Roger Bellon). The table 2 indicates the results of the antibiogram of discs charged with 20 μl of solutions with 1 mg/ml of each of the antibiotics. The solutions of blue color of bleomycin and of pepleomycin complexed with $Cu^{++}$ are prepared by addition of cupric chloride to the white solutions of bleomycin and pepleomycin. The tetracycline is employed as a control at the same concentration. In this example two strains of *Bacillus subtilis* are added. The strain 168 is well known to geneticians of bacilli, in the same way as the plasmid pUB110 which was introduced by transformation into the strain 168.

TABLE 2

Antibiogram of two isogenic strains of *Escherichia coli* and of two isogenic stains of *Bacillus subtillis* with antibiotics of the bleomycin family (antibiotic medium DIFCO n° 2 + 2 g/l glucose, pH 8, discs of 10 mm)

| Indicator strains | Phleomycin $Cu^{++}$ | Bleomycin | Bleomycin $Cu^{++}$ | Pepleomycin | Pepleomycin $Cu^{++}$ | Tetracycline |
| --- | --- | --- | --- | --- | --- | --- |
| *Escherichia coli* | | | | | | |
| HB 101 | 31 | 25 | 24 | 26 | 27 | 21 |
| HB 101 (PKC 7) | — | — | — | — | — | 22 |
| *Bacillus subtillis* | | | | | | |
| 168 | 34 | 26 | 26 | 30 | 29 | 28 |
| 168 | — | — | — | — | — | 28 |

TABLE 2-continued

Antibiogram of two isogenic strains of Escherichia coli and of two
isogenic stains of Bacillus subtillis with antibiotics of the bleomycin family
(antibiotic medium DIFCO n° 2 + 2 g/l glucose, pH 8, discs of 10 mm)

| Indicator strains | Phleomycin $Cu^{++}$ | Bleomycin | Bleomycin $Cu^{++}$ | Pepleomycin | Pepleomycin $Cu^{++}$ | Tetracycline |
|---|---|---|---|---|---|---|
| (pUB 110) | | | | | | |

It emerges very clearly from these results that the plasmid pKC7 on the one hand and the plasmid pUB110 on the other hand protect their host cells against the toxic effect of the different components of the phleomycins and of the bleomycins. The nature of the terminal amine of the bleomycin nucleus or of the phleomycin nucleus as well as the form complexed or not with the $Cu^{++}$ do not have an influence on this protection.

EXAMPLE IV

The plasmid pKC7 which results in the resistance to kanamycin and to bleomycins due to the fact of the fragment HindIII-BamHI of the transposon Tn5 is deleted from the small fragment SalI-SalI after complete digestion and ligation. The cells HB101 containing the resulting plasmid pUT2 are resistant to kanamycin but sensitive to bleomycins. The plasmid pUT3 (FIG. 1) which results from the ligation of the large fragment HindIII-SalI of pUT2 (digestion of pUT2 by SalI and HindIII and electroelution from agarose gel) and of the small fragment HindIII-XhoI of pKC7 (cleavage of pKC7 by HindIII and XhoI then electroelution) results in resistance to kanamycin and to bleomycins.

The transformation of HB101 by the DNA of the plasmid pUT3 cleaved with SpHI and then digested with Ba131 for variable times (5 min., 10 min. 20 min.) followed by addition of phosphorylated BglII linkers and BglII cleavage and then ligation gave resistant ampicillin transforming clones all sensitive to kanamycin and for about half resistant to bleomycins at 5 min times (at 10 and 20 min times all the clones were sensitive to bleomycins). The plasmid pUT37 is extracted from one of the clones sensitive to kanamycin and resistant to a high concentration of commercial bleomycin.

These results show very clearly that the gene of resistance to the bleomycins of the transposon Tn5 is distinct from that which codes for a 3' aminoside phosphotransferase of type II responsible for the resistance to kanamycin and geneticine. The sequence of the gene of structure named indifferently Tn5 Phleo$^r$ or Tn5 Bleo$^r$ is given in FIG. 2.

EXAMPLE V

The small fragment BglII-BamHI of pKC7 obtained by double digestion and electroelution of agarose gel was ligatured with the large fragment BglII-BamHI of the plasmid pUB110 of Bacillus subtilis. After transformation of the protoplastes of the strain 168 of Bacillus subtilis the clones obtained on the DM3 regeneration medium supplemented with 100 μg/ml of kanamycin were checked by their sensitivity to tobramycin (10 μg/ml, DIFCO antibiotic n°2 medium, pH 8) and their plasmid extracted. The size of the majority of the plasmids showed the expected value for the construction desired with the fragment inserted in a single direction, that where the two sites BglII and BamHI are restored (plasmid pUT100—FIG. 3). The cells of Bacillus subtilis containing the plasmid pUT100 are resistant to commercial bleomycin and to the same aminosides as those inactivated by the APH3'II of the transposon Tn5. Thus the fragment BglII-BamHI of the portion of Tn5 borne by pKC7, devoid of promoter region expresses the two types of resistance described in the structure described for this example, in Bacillus subtilis Gram+ bacteria.

In the same way, the character of resistance to commercial bleomycin can be obtained in the Streptomyces, filamentous bacteria of great importance in the fermentation industry.

The small fragment BglII-BamHI of pKC7 was inserted at the site BglII of the plasmid pIJ702 (KATZ et al., Journal of General Microbiology, 1983, 129, 2703). The hybrid plasmid resulting pUT201 (FIG. 4) characterized by double digestions results in the resistance to kanamycin and to commercial bleomycin when the latter is present in Streptomyces lividans and Stretomyces violaceoniger.

EXAMPLE VI

This example is given as an illustration of the interest of the bleomycins to select clones transformed in the case of experiments of genetic transfer in higher eucaryotic cells.

The small fragment HindIII-SalI of pUT37 is ligatured with the largest fragment HindIII-SalI of pKC7 to give the plasmid pUT6 (FIG. 5). This plasmid pUT6 is cleaved with XhoI, the adhesive ends rendered sharp by the action of Klenow polymerase and after cleavage by BglII, the small sharp-ended fragment BglII-XhoI is electroeluted from agarose gel. The fragment is ligatured with the large fragment BglII-SmaI of the plasmid pAG60 (COLBERE-GARAPIN et al., J. Mol. Biol. (1981) 150, 1) to give the plasmid pUT66 (FIG. 6).

The DNA of plasmid pUT66 is used for the transfection of the line L of deficient thymidin kinase mouse cells (TK ) by the method described by COLBERE-GARAPIN et al., Proc. Nat. Acad. Sci. USA (1979), 76, 3755). Addition of 75 μg/ml of commercial bleomycin to the growth medium results in a lethality of all the cells in 10 days of incubation. Addition of 100 μg/ml of commercial bleomycin two days after the transfection (2 μg of DNA of pUT6 per 10$^6$ cells by dish) followed by 3 weeks incubation, enables the selection of 50 clones on the average per dish transformed for the character of resistance to the bleomycin. The number of transformed clones is essentially the same when the selection is made and the two concentrations tested: 100 μg and 200 μg/ml of commercial bleomycin. It is important to indicate that when the plasmid resulting from the replacement of the fragment BglII-XhoI of pUT66 by the corresponding fragment of pKC7 is used to transfer the mouse cells, only the transformants for the resistance to geneticine (G418) but not to the bleomycins can be selected. This result is in accordance with the fact that in eukaryotes, contrary to prokaryotes cells, the translation of a polycistronic messenger RNA is not reinitiated after a translation termination codon.

EXAMPLE VII

This example is for the purpose of showing the advantage of bleomycins for the selection of transformed clones in lower eukaryotes and particularly *Saccharomyces cerevisiae*.

The large fragment EcoRI-AsuII of pKC7 obtained by EcoRI and AsuII double digestion, electroeluted from an agarose gel is treated with Klenow polymerase to transform the sticky ends into clean ends, followed by ligation. The transformation of HB101 gives clones resistant to ampicillin, weakly resistant to commercial bleomycin. The minimum inhibiting concentration of these carrier clones of the plasmid pUT8 (FIG. 7) is 0.5 µg/ml by comparison with 0.1 µg/ml for the strain HB101 and 100 µg/ml for HB101 (pKC7) in the antibiotic medium n°2+2 g of glucose, pH8. The low resistance to bleomycin resulting from the pUT8 is due to the complete loss of the promoter sequence (Pribnov box and fixation sIte of the ribosomes) in the deleted region. The EcoRI and AsuII sites are restored in this construction. The DNA of the pEX-2 plasmid (GRITZ et DAVIES, Gene (1983) 25:179) is linearized by complete digestion with BamHI. After partial digestion with EcoRI, the fragment whose size corresponds to the linear plasmid is electroeluted from an agarose gel and ligatured with the small fragment EcoRI-BamHI of pUT8. After transformation of HB101, one of the clones selected on ampicillin and resistant to 2 µg/ml of commercial bleomycin is retained as source of the plasmid pUT301 (FIG. 8).

The strain OL 1 (α, leu 2-3, leu 2-112, his 3-11, his 3-15, ura 3-251, ura 3-373, BOY MARLOTTE et JACOUET, Gene (1982) 20:433) of *Saccharomyces cerevisiae* is transformed by the DNA of pUT301 according to the method described by KLEBE et al. Gene (1983) 25:333) modified in the following manner: the cells treated with polyethylene glycol for 1 hour to 30 minutes are washed once and resuspended in 5 ml of 60% YPD-40% NB medium. After 6 hours of incubation at 30° the cells are centrifuged and the culot taken up again with 1 ml NB medium. The cells after dilution are spread with a rake either in the YNB medium supplemented with 100 µg/ml of histidine and 100 µg/ml of leucine, or in the medium DIFCO n°2+5 g/l glucose, pH 7.5, supplemented with 50 µg/ml of commercial bleomycine. After 3 days of incubation at 30° C. the number of clones transformed for the character of resistance to bleomycine is substantially the same as the number of those transformed for the character ura+ ($10^3$ transformed per µg of DNA). Check of the clones has shown on the one hand that all the ura+ clones were resistant to at least 150 µg/ml of commercial bleomycin and on the other hand the clones selected for resistance to bleomycin were all ura+.

EXAMPLE VIII

This example is intended to show that the gene of resistance to bleomycin of pUB110 is different from that which codes for the synthesis of the aminoglycoside transferase AAD 4' responsible for the resistance to kanamycin and to tobramycin.

The insertion of Sau3A fragments of the DNA of bacteriophage 4 at the site BglII of pUB110 gives clones after transformation of the protoplasts of *Bacillus subtilis* resistant to bleomycin but sensitive to kanamycin and to tobramycin (plasmids of the series pUT102). Conversely, deletion of the two smallest fragments HpAII of pUB110 (partial digestion of the DNA of pUB110 with HpaII and electroelution from an agarose gel of a band of about 3.7 kilobases closed back on itself by ligation) leads to the plasmid pUT101 which expresses in *Bacillus subtilis* the resistance to kanamycin and not to bleomycin.

EXAMPLE IX

The preceding examples have shown that two distinct genes of resistance to the antibiotics of the family of bleomycins are found carried one by the transposon Tn5 of *Escherichia coli* and on the other hand by the plasmid pUB110 of Staphylococcus and *Bacillus subtilis*. The source of resistance gene to the bleomycins is not limited to these two cases. Plasmids isolated from bacterial strains isolated in a hospitable medium may possess the information for this type of resistance. For example, the plasmid JR66 (DATTA et HEDGES, J. Gen. Microbiol. (1973) 77:11) results in the resistance to bleomycins as well as to numerous aminosides for the cells of *Escherichia coli* which harbor it.

Another origin of genes which can result in a resistance phenotype to the bleomycins is provided by the chromosomic DNA of Actinomyces producing these antibiotics. Such a gene has been cloned from the chromosomic DNA of the strain of *Streptomyces verticillius* (SV) ATCC 21890 producing phleomycins and resistance to at least 200 µg/ml of the phleomycins or of commercial bleomycine. The DNA of the strain 21890 prepared according to the method of MARMUR (J. Mol. Biol. 1961, 3:208) is purified on DEAE-cellulose then partly digested with MboI to obtain fragments comprised between 2 and 6 kilobases. The product of the ligation of these fragments with the DNA of pIJ702 opened by BglII is used to transform the protoplasts of *Streptomyces violaceoniger* according to the method described by THOMPSON et al. J. Bacteriol. (1982) 151:668. Arrest of the contacting of the protoplasts with the DNA in the presence of polyethylene glycol is done by dilution to 1/10 in a hypertonic medium and spreading at this dilution on dishes containing the non-selective R2 regeneration medium. After a week of incubation, the surface of the dishes is scraped and the spore-smycelium suspension is spread on dishes of GAPY medium supplemented with 20 µg/ml of phleomycine and 50 µg/ml of Nosiheptide (antibiotic close to thiostrepton). In the course of three separate experiments, a single stable clone, capable of developing in the presence of 20 µg of phleomycin, was isolatable. The plasmid pUT212 extracted from this clone can transform *Streptomyces violaceoniger* for the character of resistance to the phleomycins but also to other antibiotics tested: commercial bleomycin, pepleomycin, bleomycin A5 and tallysomycin.

EXAMPLE X

The transposon Tn5 functional in a large number of Gram− bacteria is very much used in molecular biology for mutagenesis experiments by insertion. The insertion of the transposon Tn5 in a chromosomic, plasmidic or phagic DNA, is followed by means of the character of resistance to kanamycin. Resistance to bleomycin can just as well be exploited for the selection. This has been checked in particular with different insertion mutants of the Tn5 in the chromosomic DNA in *Rhizobium meliloti* strain 41. All the mutants examined are shown to be resistant at the same time to kanamycin and to bleomycins. It must be pointed out that the plasmid pRme:Tn5 used for these experiments results in a resistance higher than 300 μg/ml of commercial bleomycin for the cells of the strain 41 of *Rhizobium meliloti* whereas in the absence of the plasmid the cells are killed at a concentration equal or less than 5 μg/ml in the medium TY at pH 8.

In the field of plant molecular biology the labels of resistance to the bleomycins can be shown to have great utility. Thus the cells derived from protoplasts of tobacco are killed at 1 μg/ml of commercial bleomycine in the medium C (MULLER et al., Physiol. Plant. (1983) 57:37). The gene of structure Tn5 Phleo$^r$ (FIG. 2) placed under the dependance of promoter and terminal sequences specific to plant cells should be exploitable beneficially for gene transfer in plants. A plasmid carrying the gene Tn5 Phleo$^r$ under the control of the sequences 5' and 3' not translated of nopaline synthetase has been constructed. The DNA of the plasmid pLGV23 Neo (HERRERA-ESTRELLA et al., EMBO J. (1983) 6:987) extracted from the strain of *Escherichia coli* GM 99 (dam$^-$) is linearized by BamHI and partly digested with BclI. The fragment of approximate size 6.7 kilobases is electroeluted then ligatured with the small fragment BglII-BamHI of pUT6 to give the plasmid pUT400 (FIG. 9). The cells of HB101 carrying pUT400 are weakly resistant to the bleomycins (c.m.i.:5 μg/ml of commercial bleomycin). Plasmid pUT400 should be shown to be particularly interesting for the cloning of genes in plants either by means of Agrobacterium tumefaciens or Agrobacterium rhizogenes and their respective plasmid Ti and Ri or by direct transfection of protoplasts of plant cells after encapsidation of the DNA in liposomes (CABOCHE et al., Colloque Biologie Moléculaire Végétable, ORSAY (1984) Poster p. 62).

By way of reference for the identification of the antibiotics of the family of phleomycins, the "Handbook of Antibiotic Compounds" ed. Berdy CRC press, 1980, volume 4 could be consulted.

Pepleomycin is particularly described in the article of TAKAHASHY et al., J. Antibiotics 1979, 27, 36.

We claim:

1. A method of transforming eukaryotic and prokaryotic cells sensitive to an antibiotic of the phleomycin family to confer resistance against said antibiotic, wherein the eukaryotic and prokaryotic cells are selected from the group consisting of *Escherichia coli, Bacillus subtilis*, mouse cells, *Saccharomyces cerevisiae* and *Rhizobium meliloti*, comprising:

inserting a phleo$^r$ gene of transposon Tn5, a phleo$^r$ gene of plasmid pUB110, or a phleo$^r$ SV gene of plasmid pUT212 into the eukaryotic or prokaryotic cell to transform the cell to confer resistance against the antibiotic.

* * * * *